(12) United States Patent
Ikeda et al.

(10) Patent No.: US 8,135,381 B2
(45) Date of Patent: Mar. 13, 2012

(54) MOBILE APPARATUS

(75) Inventors: Kazuhiko Ikeda, Kodaira (JP); Shiro Shimaoka, Hamura (JP); Hideki Nakashima, Hamura (JP); Noboru Imazawa, Ome (JP)

(73) Assignee: Fujitsu Toshiba Mobile Communications Limited, Kawasaki (JP)

( * ) Notice: Subject to any disclaimer, the term of this patent is extended or adjusted under 35 U.S.C. 154(b) by 539 days.

(21) Appl. No.: 12/356,662

(22) Filed: Jan. 21, 2009

(65) Prior Publication Data

US 2009/0298536 A1 Dec. 3, 2009

(30) Foreign Application Priority Data

Jun. 3, 2008 (JP) ................................ P2008-146190

(51) Int. Cl.
*H04M 11/00* (2006.01)
(52) U.S. Cl. .................... 455/405; 455/575.1; 455/414; 455/566; 455/418; 702/160
(58) Field of Classification Search ................. 455/405, 455/575.1, 414, 566, 418; 702/160
See application file for complete search history.

(56) References Cited

U.S. PATENT DOCUMENTS

| 2004/0140348 A1* | 7/2004 | Fromm | 235/105 |
| 2010/0312521 A1* | 12/2010 | Sugai | 702/160 |

FOREIGN PATENT DOCUMENTS

JP 2000-209142 A 7/2000

* cited by examiner

*Primary Examiner* — Michael Thier
*Assistant Examiner* — Julio Perez
(74) *Attorney, Agent, or Firm* — Maschoff Gilmore & Israelsen

(57) ABSTRACT

According to one aspect of the invention, there is provided a mobile apparatus including: a sensor configured to detect acceleration applied to the mobile apparatus and to generate a detection signal; a memory configured to record count data based on the detection signal, the count data associated with movement of the mobile apparatus; a counting module configured to count the number of user's steps based on the count data; a sound module configured to sound; and a counting control module configured to control the counting module to stop counting of the number of user's steps when the sound module starts sounding.

10 Claims, 4 Drawing Sheets

FIG. 1A
FIG. 1B
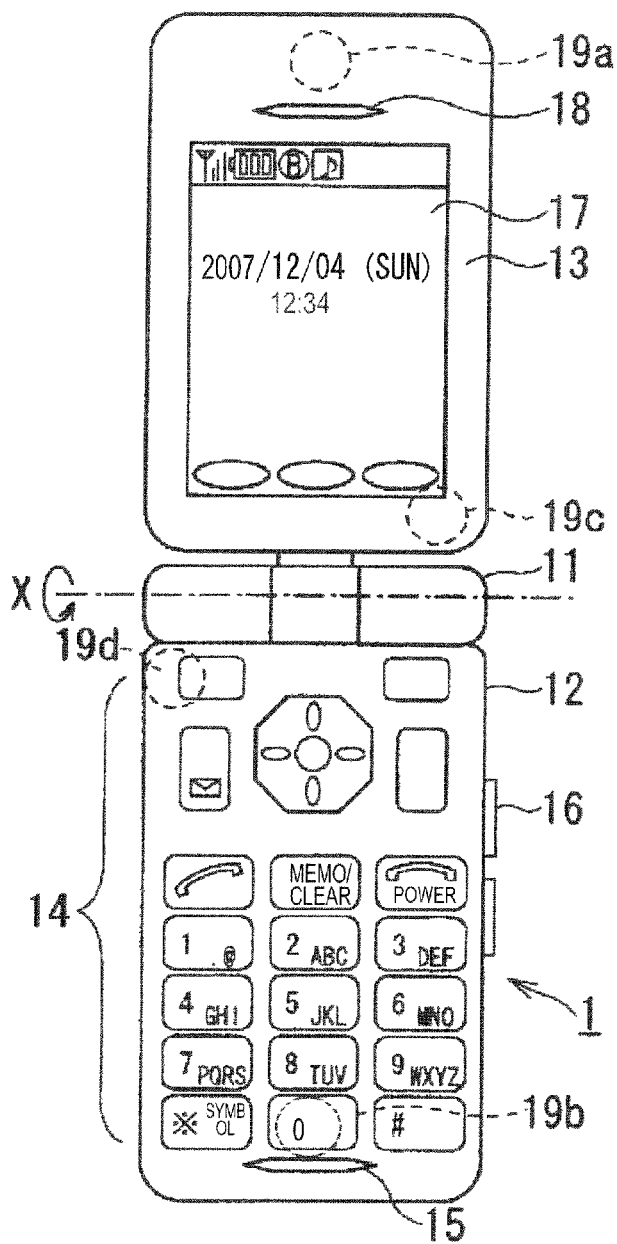
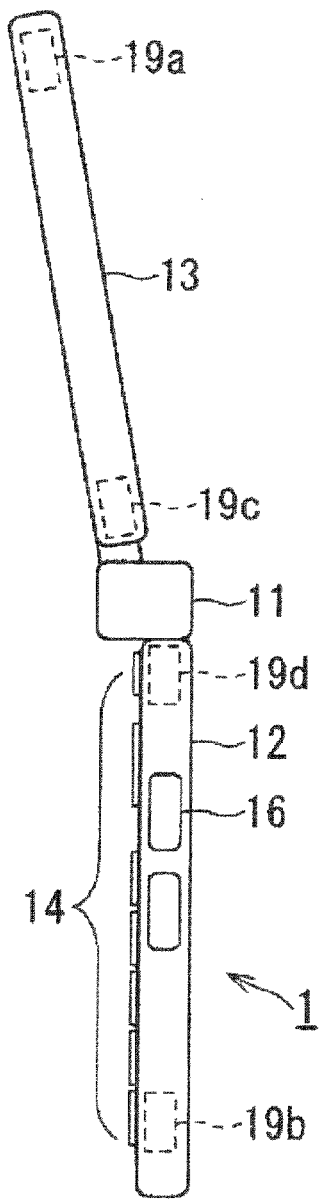

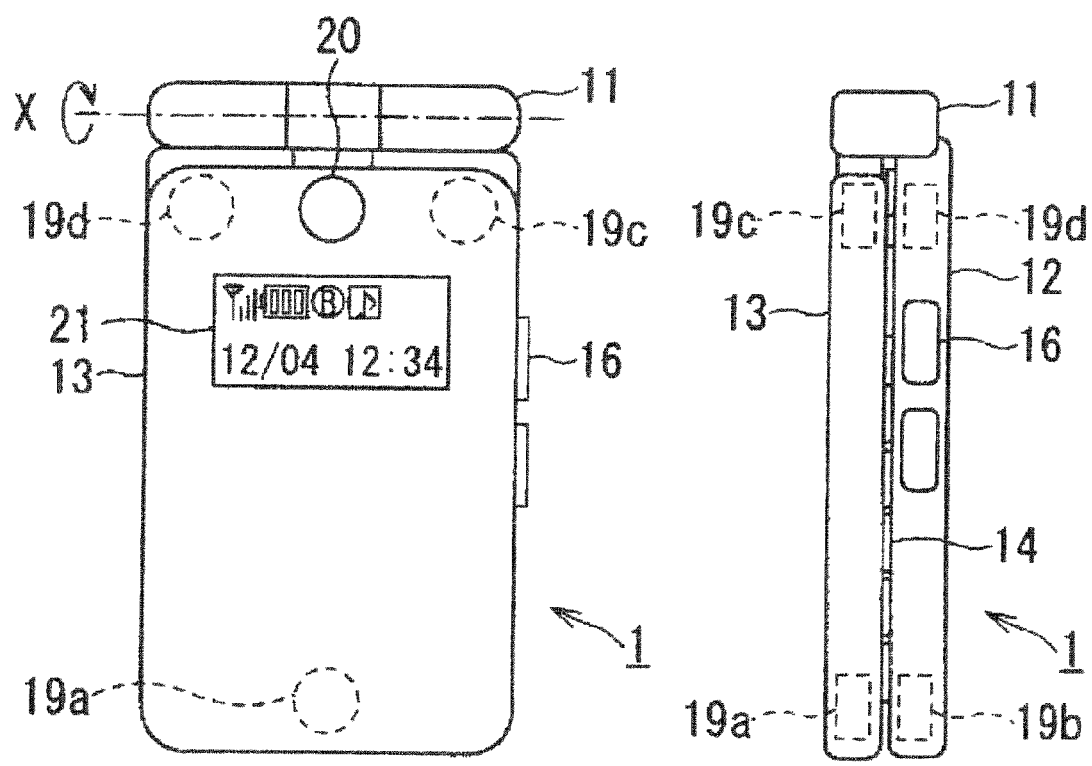

MOBILE APPARATUS

The entire disclosure of Japanese Patent Application No. 2008-146190 filed on Jun. 3, 2008 including specification, claims, drawings and abstract is incorporated herein by reference in its entirety.

BACKGROUND

1. Field of the Invention

One aspect of the present invention relates to a mobile apparatus and particularly relates to a mobile apparatus equipped with an acceleration sensor.

2. Description of the Related Art

A mobile phone as a mobile apparatus has been recently equipped not only with a simple communication function like telephone call but also with an address book function, a mail function via a base station or via a network such as the internet, a browser function for making it possible to browse a Web page etc., a music control function for making it possible to listen to audio data, a function for making it possible to receive terrestrial digital one-segment broadcast wave, etc.

On the other hand, there is proposed a technique using the mobility of the mobile phone to provide an acceleration sensor incorporated in the mobile phone to give a pedometer function to the mobile phone. The following technique is known as a technique associated with a pedometer (see JP-A-2000-209142, for instance). According to the technique proposed in JP-A-2000-209142, a value of the number of steps of user's walking is measured and stored in a memory so that the integrated value of the stored value and a set step count value can be displayed as a walking distance, that a user can be informed of an alarm or the counting of the number of steps can be stopped temporarily when the value of the number of steps corresponds to a set target value, and that the value of the number of steps stored in the memory can be read to perform continuous measurement of the walking distance when the measurement needs to be resumed.

Generally, a high-grade step count misrecognition prevention function was not provided in the acceleration sensor incorporated in the mobile phone. For this reason, when a speaker of the mobile phone made any sound, slight vibration was caused by the speaker's sounding. As a result, the acceleration sensor incorporated in the mobile phone detected acceleration generated in the mobile phone based on the vibration. There was a problem that the number of user's steps was counted though the user did not walk.

SUMMARY

According to one aspect of the invention, there is provided a mobile apparatus including: a sensor configured to detect acceleration applied to the mobile apparatus and to generate a detection signal; a memory configured to record count data based on the detection signal, the count data associated with movement of the mobile apparatus; a counting module configured to count the number of user's steps based on the count data; a sound module configured to sound; and a counting control module configured to control the counting module to stop counting of the number of user's steps when the sound module starts sounding.

BRIEF DESCRIPTION OF THE DRAWINGS

Embodiment may be described in detail with reference to the accompanying drawings, in which:

FIGS. 1A and 1B are exemplary views showing a visual configuration of a mobile phone which can be used as a mobile apparatus according to the invention;

FIGS. 2A and 2B are exemplary views showing another visual configuration of the mobile phone which can be used as a mobile apparatus according to the invention;

DETAILED DESCRIPTION OF THE EMBODIMENTS

Figure 3:
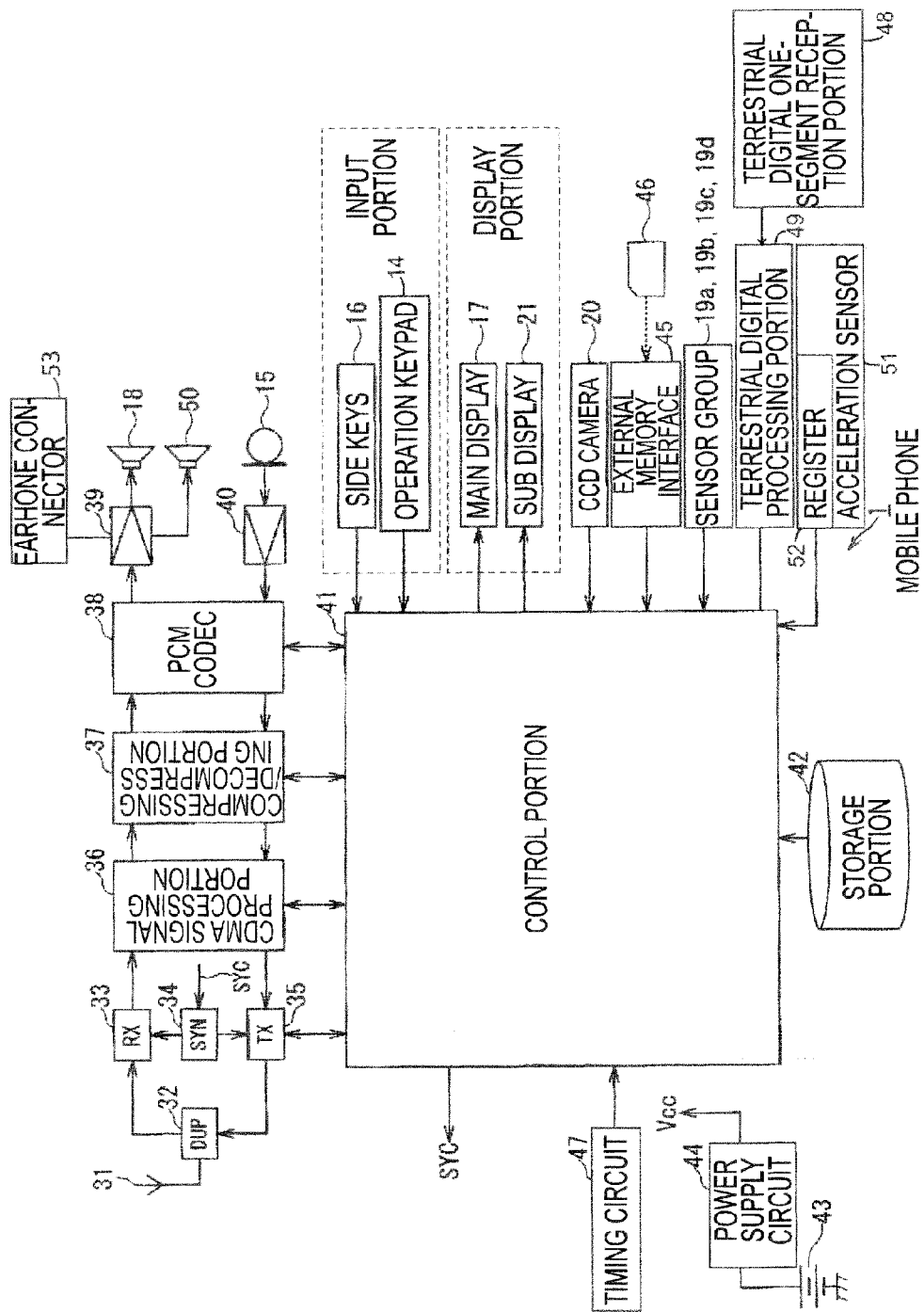
FIG. 3 is an exemplary block diagram showing the internal configuration of the mobile phone which can be used as a mobile apparatus according to the invention.

An embodiment of the invention will be described below with reference to the drawings. FIGS. 1A and 1B show a visual configuration of a mobile phone 1 which can be used as a mobile apparatus according to the invention. FIG. 1A is a front view showing the visual configuration of the mobile phone 1 unfolded at an open angle of about 180 degrees. FIG. 1B is a side view showing the visual configuration of the unfolded mobile phone 1.

As shown in FIGS. 1A and 1B, the mobile phone 1 has a hinge portion 11 disposed in the center of the mobile phone 1, and first and second casings 12 and 13 which are connected to each other by the hinge portion 11 as the boundary between the first and second casings 12 and 13 so that the mobile phone 1 can be folded in the direction of an arrow X through the hinge portion 11. A transmission/reception antenna (antenna 31 in FIG. 3 which will be described later) is incorporated in a position of the inside of the mobile phone 1 so that the mobile phone 1 exchanges electric wave with a base station (not shown) through the internal antenna.

An operation keypad 14 including numeric keys "0" to "9", a call key, a redial key, a call off/power key, a clear key and an e-mail key is provided in a surface of the first casing 12. The operation keypad 14 can be used for inputting various instructions.

In the first casing 12, the operation keypad 14 further includes a cross key and a determination key. When a user operates the cross key up, down, left and right, the cursor can be moved in the key's designated direction. Specifically, the user can perform various operations such as a scrolling operation of a phone number list or an e-mail displayed on a main display 17 provided in the second casing 13, a page turning operation of a simplified website, and an image sending operation.

When the user presses down the determination key, various functions can be determined. When, for example, a desired phone number is selected from phone numbers in a phone number list displayed on the main display 17 according to a user's operation at the cross key in the first casing 12 and the determination key is pressed down toward the inside of the first casing 12, the selected phone number is determined and a calling process is performed on the determined phone number.

In the first casing 12, the e-mail key is provided on the left side of the cross key and the determination key. When the e-mail key is pressed down toward the inside of the first casing 12, a mail transmission/reception function can be called. A browser key is provided on the right side of the cross key and the determination key. When the browser key is pressed down toward the inside of the first casing 12, data of a Web page can be browsed.

In the first casing 12, a microphone 15 is provided in a lower portion of the operation keypad 14. User's voice during conversation is collected by the microphone 15. Side keys 16 for operating the mobile phone 1 are further provided in the first casing 12.

Incidentally, a battery pack not shown is attached to the back side of the first casing 12. When the call off/power key is turned on, the battery pack supplies electric power to respective circuit portions so that the respective circuit portions are actuated in an operable state.

On the other hand, the main display 17 is provided in a front surface of the second casing 13. The main display 17 can be used for displaying not only the electric wave receiving condition, the residual battery amount, names and phone numbers registered as a phone book and the transmission history but also content data of an e-mail, a simplified website, an image taken by a Charge Coupled Device (CCD) camera (CCD camera 20 shown in FIG. 2A which will be described later), content data received from an external content data server (not shown) and content data recorded on a memory card (memory card 46 in FIG. 3 which will be described later) A receiver (telephone receiver) 18 is provided in a position of an upper portion of the main display 17. The user can receive a telephone message as voice from the receiver 18. As shown in FIG. 3, a speaker 50 and an earphone connector 53, which are another audio output portion, are provided with the mobile phone 1. When earphones are not connected to the earphone connector 53, voice on the phone call is output from the receiver 18 and audio such as ringtone is output from the speaker 50. In contrast, when the earphones are connected to the earphone connector 53, audio including both voice on the phone call and ringtone is output from the earphones.

Magnetic sensors 19a, 19b, 19c and 19d for detecting a status of the mobile phone 1 are provided in inner positions of the first and second casings 12 and 13. The main display 17 may be a display formed from organic EL or may be a Liquid Crystal Display (LCD).

FIGS. 2A and 2B show another visual configuration of the mobile phone 1 which can be used as a mobile apparatus according to the invention. The state of the mobile phone 1 shown in FIGS. 2A and 2B is a state where the mobile phone 1 shown in FIGS. 1A and 1B is rotated in the direction of the arrow X. That is, FIG. 2A is a front view showing the visual configuration of the folded mobile phone 1, and FIG. 2B is a side view showing the visual configuration of the folded mobile phone 1.

A CCD camera 20 is provided in an upper portion of the second casing 13. An image of a desired subject can be taken by the CCD camera 20. A sub-display 21 is provided below the CCD camera 20. The sub-display 21 is used for displaying an antenna picture indicating the current sensitivity level of the antenna, a battery picture indicating the current residual amount of the battery of the mobile phone 1, the current time, etc.

FIG. 3 shows the internal configuration of the mobile phone 1 which can be used as a mobile apparatus according to the invention. A radio signal transmitted from a base station not shown is received by the antenna 31 and then input to a reception circuit (RX) 33 through an antenna duplicator (DUP) 32. The reception circuit 33 down-converts the received radio signal into an intermediate frequency signal by mixing the radio signal with a local oscillation signal output from a frequency synthesizer (SYN) 34. Then, the reception circuit 33 outputs a received baseband signal by quadrature demodulation of the down-converted intermediate frequency signal. The frequency of the local oscillation signal generated by the frequency synthesizer 34 is designated by a control signal SYC output from a control portion 41.

The received baseband signal output from the reception circuit 33 is input to a CDMA signal processing portion 36. The CDMA signal processing portion 36 has a RAKE receiver not shown. The RAKE receiver performs spectrum despreading of paths included in the received baseband signal with respective spreading codes (i.e. spreading codes the same as the spreading codes of spreaded received signals). Then, signals of the despreaded paths are subjected to phase arbitration and then subjected to coherent Rake combination. A Rake combined data series is subjected to deinterleaving and channel decoding (error correction decoding) and then subjected to two-value data determination. As a result, received packet data of a transmission format is obtained. The received packet data is input to a compressing/decompressing portion 37.

The compressing/decompressing portion 37 has a Digital Signal Processor (DSP). The received packet data output from the CDMA signal processing portion 36 is separated according to media by a multiplexing/demultiplexing portion not shown. The data separated according to media are decoded. For example, in a telephone call mode, audio data corresponding to conversation voice etc. contained in the received packet data is decoded with a speech codec. For example, in a mode such as a television telephone mode, when motion picture data is contained in the received packet data, the motion picture data is decoded with a video codec. In addition, when the received packet data is downloaded content data, the downloaded content data are decompressed and then the decompressed downloaded content data are output to the control portion 41.

A digital audio signal obtained by the decoding process is fed to a PCM codec 38. The PCM codec 38 PCM-decodes the digital audio signal output from the compressing/decompressing portion 37 and outputs the PCM-decoded analog audio signal to a reception amplifier 39. The analog audio signal is amplified by the reception amplifier 39 and then output from the receiver 18.

A digital motion picture signal decoded with the video codec by the compressing/decompressing portion 37 is input to the control portion 41. The control portion 41 controls the main display 17 to display a motion picture based on the digital motion picture signal output from the compressing/decompressing portion 37, through a video RAM (e.g. VRAM) not shown. The control portion 41 can control the main display 17 to display not only the received motion picture data but also a motion picture data taken by the CCD camera 20, through the video RAM not shown.

When the received packet data is an e-mail, the compressing/decompressing portion 37 feeds the e-mail to the control portion 41. The control portion 41 controls a storage portion 42 to store the e-mail fed from the compressing/decompressing portion 37. Then, the control portion 41 reads the e-mail stored in the storage portion 42 to display the read e-mail on the main display 17 according to a user's operation of the operation keypad 14 as an input portion.

On the other hand, in a telephone call mode, a speaker's (user's) voice signal (analog audio signal) input to the microphone 15 is amplified to a proper level by a transmission amplifier 40 and then PCM-coded by the PCM codec 38. The PCM-coded digital audio signal is input to the compressing/decompressing portion 37. A motion picture signal output from the CCD camera 20 is digitized by the control portion 41 and then input to the compressing/decompressing portion 37.

An e-mail as text data generated by the control portion 41 is also input to the compressing decompressing portion 37.

The compressing/decompressing portion 37 compression-codes the digital audio signal output from the PCM codec 38, based on a format in accordance with a predetermined transmission data rate. As a result, audio data is generated. Moreover, the compressing/decompressing portion 37 generates motion picture data by compression-coding the digital motion picture signal output from the control portion 41. Then, the compressing/decompressing portion 37 multiplexes and packetizes these audio data and motion picture data in accordance with a predetermined transmission format by using a multiplexing/demultiplexing portion not shown and outputs the packetized transmission packet data to the CDMA signal processing portion 36. Also when an e-mail is output from the control portion 41, the compressing/decompressing portion 37 multiplexes the e-mail into transmission packet data.

The CDMA signal processing portion 36 applies a spectrum spreading process using spreading codes allocated to transmission channels to the transmission packet data output from the compressing/decompressing portion 37 and outputs the spectrum-despreaded output signal to a transmission circuit (TX) 35. The transmission circuit 35 modulates the spectrum-despreaded signal by using a digital modulation method such as a Quadrature Phase Shift Keying (QPSK) method. The transmission circuit 35 up-converts the digital modulated transmission signal into a radio signal by combining the digital modulated transmission signal with a local oscillation signal generated from the frequency synthesizer 34. Then, the transmission circuit 35 high-frequency amplifies the radio signal generated by the up-conversion so that the level of the radio signal reaches a transmission power level designated by the control portion 41. The high-frequency amplified radio signal is fed to the antenna 31 through the antenna duplicator 32 and transmitted from the antenna 31 toward a base station not shown.

The mobile phone 1 further has an external memory interface 45. The external memory interface 45 has a slot into which a memory card 46 can be detachably attached. The memory card 46 is a kind of flash memory card such as an NAND flash memory card or an NOR flash memory card cited as a representative example. The memory card 46 is formed so that various data such as image, voice, audio, etc. can be written and read through a 10-pin terminal. A timing circuit (timer) 47 for measuring the current time accurately is further provided in the mobile phone 1.

The control portion 41 has a Central Processing Unit (CPU), a Read Only Memory (ROM), and a Random Access Memory (RAM). The CPU performs various processes according to programs stored in the ROM or various application programs including an operating system (OS) loaded into the RAM from the storage portion 42. The CPU generates various control signals and feeds the control signals to the respective portions to thereby generally control the mobile phone 1. The RAM temporarily stores data or the like necessary for the CPU to perform various processes. Incidentally, the control portion 41 has one CPU or a plurality of CPUs as occasion demands.

The storage portion 42 is made of an electrically rewritable/erasable nonvolatile memory such as a flash memory device or a Hard Disc Drive (HDD). The storage portion 42 stores various data sets and various application programs to be performed by the CPU of the control portion 41.

A power supply circuit 44 generates a voltage source Vcc based on the output of a battery 43 and supplies the voltage source Vcc to respective circuit portions. A terrestrial digital one-segment reception portion 48 receives terrestrial digital one-segment broadcast wave or terrestrial digital radio broadcast wave from a broadcast station not shown, and feeds a Transport Stream (TS) signal based on the received terrestrial digital one-segment broadcast wave or terrestrial digital radio broadcast wave to a terrestrial digital processing portion 49. When terrestrial digital one-segment broadcast wave is received by the terrestrial digital one-segment reception portion 48, the terrestrial digital processing portion 49 separates the TS signal based on the terrestrial digital one-segment broadcast wave from the terrestrial digital one-segment reception portion 48, into Elementary Streams (ESs) as audio data and video data, decodes the separated audio data by a predetermined decoding method in an audio decoder (not shown) provided in the terrestrial digital processing portion 49, decodes the separated video data by a predetermined decoding method in a video decoder (not shown) provided in the terrestrial digital processing portion 49, and feeds the decoded digital audio and video signals to the control portion 41.

An acceleration sensor 51 detects acceleration generated in the mobile phone 1 and generates a detection signal. Specifically, the acceleration sensor 51 determines whether amplitude expressing acceleration generated in the mobile phone 1 is larger than a predetermined reference value set in advance or not. When determination is made that amplitude expressing acceleration generated in the mobile phone 1 is larger than a reference value set in advance, the acceleration sensor 51 generates a detection signal indicating that acceleration generated in the mobile phone 1 has been detected. Then, the acceleration sensor 51 records count data on a register 52 incorporated in the acceleration sensor 51, based on the generated detection signal. The count data includes: data associated with the number of detections of acceleration applied to the mobile phone 1 (i.e. the number of user's steps) in a period of from a point of time when count data was read from the acceleration sensor by the CPU of the control portion 41 to a point of time when next count data has been read; and data associated with the detected time. The power of the acceleration sensor 51 is always set to be ON.

The CPU of the control portion 41 operates intermittently for the sake of power saving. In a sleep state, the CPU of the control portion 41 operates intermittently to detect presence of an incoming call. Whenever this operation is made, the CPU of the control portion 41 reads count data recorded on the register 52 of the acceleration sensor 51, and counts up the number of user's steps based on the read count data. Of course, when the CPU of the control portion 41 does not operate intermittently, the step count-up process may be performed whenever the acceleration sensor 51 detects acceleration generated in the mobile phone 1 and generates a detection signal in order to attach more importance to the real time property of the user's step count-up, or the count-up process may be performed collectively for a certain large quantity (at intervals of a time).

Figure 4:
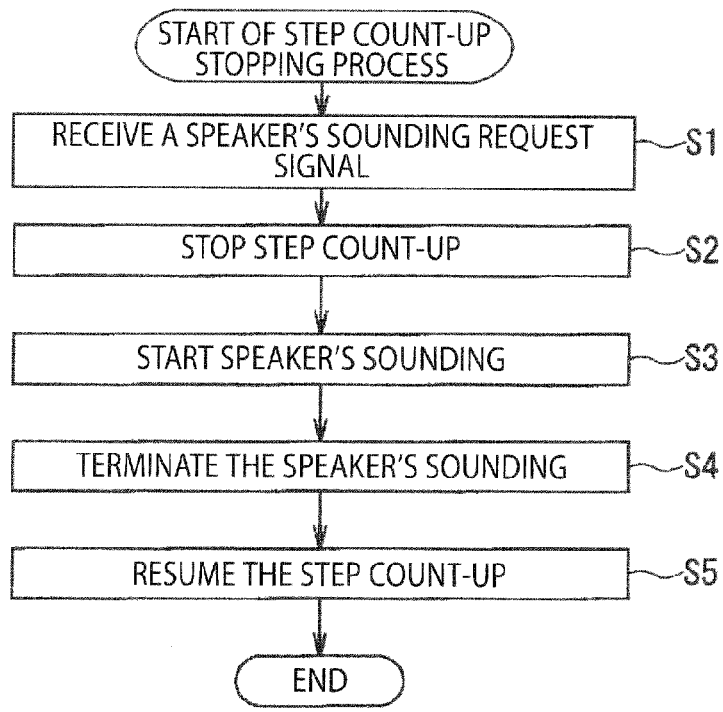
FIG. 4 is an exemplary flow chart for explaining a step count-up stopping process in the mobile phone shown in FIG. 3.

Incidentally, a high-grade step count misrecognition prevention function is not provided generally in the acceleration sensor 51 incorporated in the mobile phone 1. For this reason, when the speaker 50 of the mobile phone 1 makes any sound, slight vibration is caused by the speaker's sounding. As a result, the acceleration sensor 51 incorporated in the mobile phone 1 detects acceleration generated in the mobile phone 1 based on the vibration, so that the number of user's steps is counted though the user does not walk. Therefore, in the embodiment, the count-up process based on count data by the acceleration sensor 51 is stopped during a period between start and end of the speaker 50's sounding. As a result, occurrence of miscounting of the number of user's steps can be preferably prevented so that accuracy in counting of the number of steps can be improved. A step count-up stopping process using this method will be described below. When the earphones are connected to the earphone connector 53, an earphone sound request signal requesting sounding from the earphones via the earphone connector 53 is output and sound is output from not the speaker 50 but the earphones. In this case, the step count-up stopping process shown in FIG. 4 is not performed.

A step count-up stopping process in the mobile phone 1 shown in FIG. 3 will be described with reference to FIG. 4 which is a flow chart of the process. In FIG. 4, the step count-up stopping process is based on the assumption that the CPU of the control portion 41 does not operate intermittently.

In step S1, the control portion 41 receives an incoming call signal from another mobile phone 1 or the like through the antenna 31 or the like, and receives a speaker 50's sounding request signal on an incoming call. The speaker 50's sounding request signal is a signal for requesting sounding from the speaker 50. In step S2, the control portion 41 recognizes that a sounding process based on the speaker 50's sounding request signal will be performed afterward, and temporarily stops the step count-up performed at a timing that the detection signal is generated by the acceleration sensor 51, or the like. That is, even when the acceleration sensor 51 detects acceleration in the mobile phone 1 and generates a detection signal, the step count-up process is not performed so that counting based on the detection signal generated by the acceleration sensor 51 is not reflected on the number of steps as long as Step 2 in the step count-up stopping process continues.

In step S3, the control portion 41 controls the PCM codec 38 or the like based on the received speaker 50's sounding request signal to start a sounding of the speaker 50. In step S4, the control portion 41 controls the PCM codec 38 or the like to terminate the sounding of the speaker 50 when, for example, a call-off instruction is received according to a user's operation at the operation keypad 14.

In step S5, the control portion 41 recognizes the termination of the sounding process based on the speaker 50's sounding request signal, cancels the step count-up stopping process because there is no risk of miscounting of the number of steps caused by the sounding, and resumes the step count-up at a timing that the detection signal is generated by the acceleration sensor 51, or the like.

The step count-up stopping process using the flow chart of FIG. 4 is designed so that the step count-up stopping process is performed when the speaker 50's sounding request signal is received. However, the invention is not limited to this case. For example, the invention may be applied to a case where audio playback using the speaker 50 is performed. A step count-up stopping process in this case is shown in a flow chart of FIG. 5.

Figure 5:
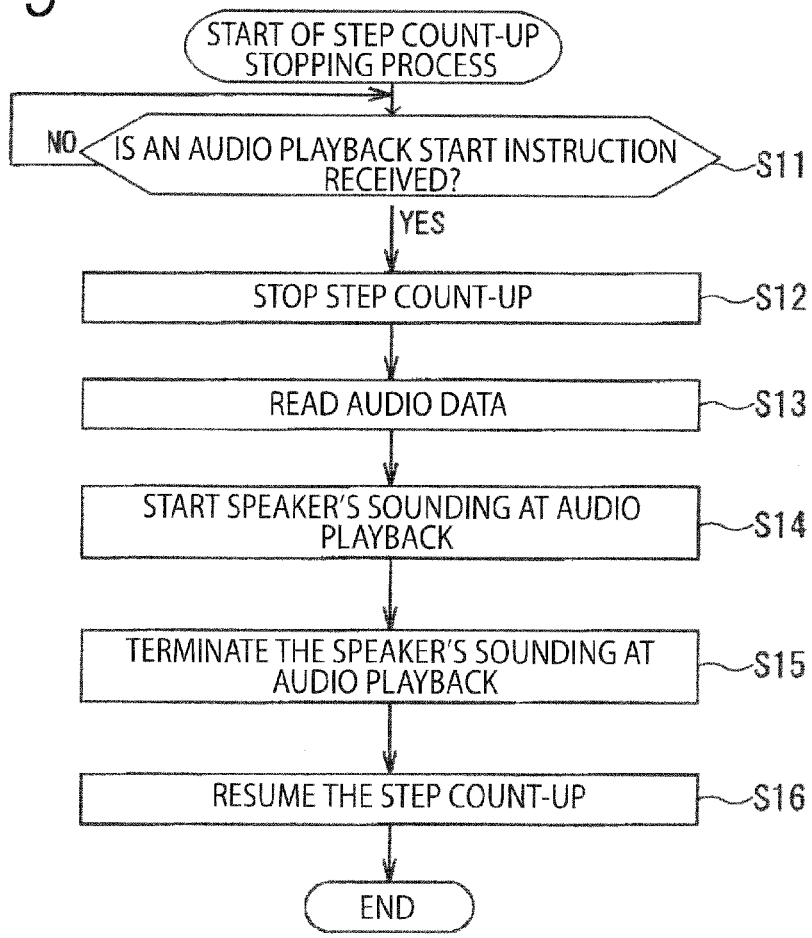
FIG. 5 is an exemplary flow chart for explaining another step count-up stopping process in the mobile phone shown in FIG. 3.

Another step count-up stopping process in the mobile phone 1 shown in FIG. 3 will be described with reference to the flow chart of FIG. 5. The process shown in FIG. 5 is basically the same as the process shown in FIG. 4, so that repetition of description thereof will be omitted.

In step S11, the control portion 41 determines whether an audio playback start instruction based on a user's operation at the operation keypad 14 on a menu screen is received or not, and waits for the reception of the audio playback start instruction. When the control portion 41 determines in the step S11 that the audio playback start instruction is received, processing goes to step S12. In the step S12, the step count-up stopping process is performed. The step count-up stopping process in the step S12 is the same as the step count-up stopping process in the step S2 in FIG. 4, so that repetition of description thereof will be omitted.

In step S13, the control portion 41 reads audio data stored in advance in the storage portion 42 and cuts the read audio data by a frame of a data size. Then, the control portion 41 decodes the extracted audio data frames successively by a decoding method. In step S14, the control portion 41 controls the PCM codec 38 or the like to start speaker 50's sounding at audio playback by using the decoded audio data. In step S15, the control portion 41 controls the PCM codec 38 or the like to terminate the sounding of the speaker 50 when, for example, an audio playback termination instruction is received according to a user's operation at the operation keypad 14. Then, processing goes to step S16. In the step S16, the step count-up stopping process is cancelled and the step count-up process is resumed.

In the embodiment of the invention, acceleration in the mobile phone 1 is detected and a detection signal is generated. Count data associated with the number of user's steps according to movement of the mobile phone 1 is recorded based on the generated detection signal. The number of user's steps is counted based on the recorded count data. When sounding is started, the counting unit's counting of the number of user's steps can be stopped. Accordingly, occurrence of miscounting of the number of user's steps can be preferably prevented, so that accuracy in counting of the number of steps can be improved even in a situation that misrecognition of the number of steps may occur.

The invention can be applied not only to the mobile phone 1 but also to another mobile apparatus such as a Personal Digital Assistant (PDA), a personal computer, a portable game player, a portable audio player, a portable video player, etc.

The series of processes described in the embodiment of the invention may be performed by software or may be performed by hardware.

Although the embodiment of the invention has been described on the case where the steps of each flow chart are performed in time series of the described order, the steps need not be performed in time series. That is, the invention can be applied to the case where the steps are performed in parallel or individually.

What is claimed is:

1. A mobile apparatus comprising:
   a sensor configured to detect acceleration applied to the mobile apparatus and to generate a detection signal;
   a memory configured to record count data based on the detection signal, the count data associated with movement of the mobile apparatus;
   a counting module configured to count the number of user's steps based on the count data;
   a sound module configured to sound; and
   a counting control module configured to control the counting module to stop counting of the number of user's steps when the sound module starts sounding,
   wherein the counting control module is configured to control the counting module to stop counting of the number of user's steps when the sound module starts sounding based on a sound request signal on an incoming call.

2. The mobile apparatus of claim 1, wherein the counting control module is configured to resume counting of the number of user's steps when the sound module terminates sounding.

3. The mobile apparatus of claim 1, wherein the counting control module is configured to control the counting module to stop counting of the number of user's steps when the sound module starts sounding based on an instruction to start audio playback.

4. The mobile apparatus of claim 1, wherein the counting control module is configured:
to receive a sound request signal;
to control the counting module to stop counting; and
to control the sound module to start sounding.

5. The mobile apparatus of claim 1, wherein the counting control module is configured:
to receive an instruction to start audio playback;
to control the counting module to stop counting; and
to control the sound module to start sounding.

6. A mobile apparatus comprising:
a sensor configured to detect acceleration applied to the mobile apparatus and to generate a detection signal;
a memory configured to record count data based on the detection signal, the count data associated with movement of the mobile apparatus;
a counting module configured to count the number of user's steps based on the count data;
a key module;
a sound module configured to sound based on an instruction from the key module; and
a counting control module configured to control the counting module to stop counting of the number of user's steps when the sound module starts sounding,
wherein the counting control module is configured to control the counting module to stop counting of the number of user's steps when the sound module starts sounding based on a sound request signal on an incoming call.

7. The mobile apparatus of claim 6, wherein the counting control module is configured to resume counting of the number of user's steps when the sound module terminates sounding.

8. The motile apparatus of claim 6, wherein the counting control module is configured to control the counting module to stop counting of the number of user's steps when the sound module starts sounding based on an instruction to start audio playback.

9. The mobile apparatus of claim 6, wherein the counting control module is configured:
to receive a sound request signal;
to control the counting module to stop counting; and
to control the sound module to start sounding.

10. The mobile apparatus of claim 6, wherein the counting control module is configured:
to receive an instruction to start audio playback;
to control the counting module to stop counting; and
to control the sound module to start sounding.

\* \* \* \* \*